United States Patent [19]

Rencher

[11] Patent Number: 5,462,749
[45] Date of Patent: Oct. 31, 1995

[54] BIOADHESIVE PHARMACEUTICAL CARRIER

[75] Inventor: William F. Rencher, Devon, Pa.

[73] Assignee: McNeil-PPC, Inc., Milltown, N.J.

[21] Appl. No.: 220,314

[22] Filed: Apr. 26, 1994

Related U.S. Application Data

[62] Division of Ser. No. 991,696, Dec. 16, 1992, Pat. No. 5,314,915, which is a division of Ser. No. 766,493, Sep. 25, 1991, Pat. No. 5,192,802.

[51] Int. Cl.$^6$ .............................. A61K 9/02; A61K 9/06; A61K 47/00; A61L 15/03
[52] U.S. Cl. ................... 424/484; 424/485; 424/488; 514/779; 514/781; 514/782; 514/944
[58] Field of Search ........................ 424/484, 485, 424/488; 514/944, 779, 781, 782

[56] References Cited

U.S. PATENT DOCUMENTS

| | | | |
|---|---|---|---|
| 3,257,276 | 6/1966 | Broh-Kahn et al. | 514/159 |
| 4,241,048 | 12/1980 | Durbak et al. | 514/335 |
| 4,292,299 | 9/1981 | Suzuki et al. | 424/16 |
| 4,518,721 | 5/1985 | Dhabhan et al. | 523/120 |
| 4,659,696 | 4/1989 | Shin-ichiro | 514/15 |
| 4,844,902 | 7/1989 | Orohe | 414/449 |
| 4,867,970 | 9/1989 | Newsham et al. | 424/435 |
| 4,894,232 | 1/1990 | Reul et al. | 424/439 |
| 4,915,948 | 4/1990 | Gallopo et al. | 424/435 |
| 4,981,815 | 1/1991 | Leusner et al. | 514/774 |
| 4,989,607 | 2/1991 | Klusch et al. | 128/610 |
| 4,999,342 | 3/1991 | Ahman et al. | 424/432 |
| 5,009,881 | 4/1991 | Hill et al. | 424/49 |
| 5,057,306 | 10/1991 | Hill et al. | 514/901 |
| 5,057,307 | 10/1991 | Hill et al. | 514/901 |
| 5,059,189 | 10/1991 | Cilento et al. | 604/307 |
| 5,192,802 | 3/1993 | Rencher | 514/535 |
| 5,292,512 | 3/1994 | Schaefer et al. | 424/401 |
| 5,314,915 | 5/1994 | Rencher | 514/535 |

FOREIGN PATENT DOCUMENTS

| | | | |
|---|---|---|---|
| 288945 | 4/1988 | European Pat. Off. . | |
| 307599 | 8/1988 | European Pat. Off. . | |
| 336901 | 10/1989 | European Pat. Off. . | |
| 6011631 | 6/1985 | Japan . | |
| 1279838 | 11/1989 | Japan . | |
| 979909 | 1/1965 | United Kingdom | 514/901 |
| 2181957 | 5/1981 | United Kingdom | 514/901 |
| 90/12588 | 11/1910 | WIPO | 514/901 |
| 89/10117 | 11/1989 | WIPO | 514/901 |

OTHER PUBLICATIONS

Gurnly et al Biomaterials 5(6): 336–340(1984) Bioadhesive Intraoral Release Systems.
Grosllj et al, Aoboz Vrav. Vesin. 36(314): 71(1981).
Mofen Son et al. Clin. Pediatr. 22(3): 190–192(1983).
N. Peppas, "Surface, Interfacial and Molecular Aspects of Polymer Bioadhesion on Soft Tissues," J. of Controlled Release, 2, (1985) pp. 257–275.
N. Peppas, (Ed.,) Hydrogels in Medicine and Pharmacy, vol. III, Chapter 8, (1987) pp. 151–175.
H. Park "Physico–Chemical Properties of Water Insoluble Polymers Important to Muchin/Epithelial Adhesion", J. of Controlled Release, 2, (1985) pp. 47–57.
Adhesion in Biological Studies, R. Manly, Ed. Chapter 10, 1970, pp. 163–181.

*Primary Examiner*—Shep Rose
*Attorney, Agent, or Firm*—Bernard F. Plantz

[57] ABSTRACT

Bioadhesive pharmaceutical carrier consisting essentially of a polymer blend of sodium carboxymethyl cellulose and xanthan gum or sodium alginate. The invention also provides for a method of control releasing a pharmaceutical active comprising incorporating an active into the bioadhesive pharmaceutical carrier. The invention is particularly adaptable for oral use and teething gels.

7 Claims, No Drawings

BIOADHESIVE PHARMACEUTICAL CARRIER

This is a division of application Ser. No. 07/991,696, filed Dec. 16, 1992, U.S. Pat. No. 5,314,915 which is a division of application Ser. No. 07/766,495, filed Sep. 25, 1991, now U.S. Pat. No. 5,192,802, all of which are hereby incorporated by reference.

FIELD OF THE INVENTION

This invention relates to bioadhesive pharmaceutical carriers. More specifically, the pharmaceutical carrier is a liquid gel matrix comprising a particular polymer blend.

BACKGROUND OF THE INVENTION

Topical chemotherapeutic treatment of mucous membranes or other moist areas of the human body is problematic because of the inherent challenge of maintaining the localization of the pharmaceutical at the point of contact. In the mouth area, for example, in the cheeks, gums, tongue, or pallet area, as well as the lips, it is difficult to maintain a presence of a topically applied pharmaceutical because of its tendency to wash away with the patient's saliva and movements of the mouth which are normally present. While various bioadhesive formulations have been proposed for application to such moist areas, they have not been completely successful and there exists the need for additional bioadhesive pharmaceutical carrier materials for application to mucous membrane and other moist body areas.

For example, Gallopo et al. in U.S. Pat. No. 4,915,948 have developed a tablets for bioadhesion to mucous membranes. The tablets comprise effective amounts of a water soluble biopolymer selected from the group consisting of a xanthan gum, a pectin, and mixtures thereof and a solid polyol. The polyol may be a sugar alcohol such as sorbitol or xylitol. Various pharmaceutical additives can be provided in such a tablet to provide for a controlled release of such pharmaceutical actives. It is the object of the present invention to provide a more convenient bioadhesive pharmaceutical carrier that can be applied to mucous membrane and other moist body areas which is in a gel form that not only provides good bioadhesion but also control release of pharmaceuticals therefrom.

SUMMARY OF THE INVENTION

It is therefore an object of the present invention to provide a bioadhesive pharmaceutical carrier in liquid gel matrix form for application to mucous membranes and other moist body parts for the controlled release of pharmaceutical actives thereto.

As embodied and fully described herein, the present invention provides a bioadhesive pharmaceutical carrier consisting essentially of a polymer blend of sodium carboxymethyl cellulose and xanthan gum or sodium alginate. In other embodiments the invention provides bioadhesive pharmaceutical dosage form in solid or semi-solid form consisting essentially of an effective amount of a pharmaceutical active composition dispensed in a polymer blend of sodium carboxymethyl cellulose and xanthan gum. Preferably, the bioadhesive dosage form is in semi-solid form and comprises from about 0.25% to 50% sodium carboxymethyl cellulose and xanthan gum or sodium alginate and from about 0.25 to 50% of these components by weight of the total weight of the pharmaceutical product.

In preferred embodiments, the dosage form additionally comprises a water soluble viscous vehicle material. In other embodiments, the bioadhesive dosage form additionally comprises a viscous vehicle material which has low water solubility or is water insoluble.

In a preferred embodiment, the invention comprises a teething gel product comprising a bioadhesive pharmaceutical carrier and an anesthetic. In other embodiments, the invention comprises a method of control releasing a pharmaceutical active comprising incorporating the active in a bioadhesive pharmaceutical carrier comprising a polymer blend of sodium carboxymethyl cellulose and xanthan gum or sodium alginate.

DETAILED DESCRIPTION OF PREFERRED EMBODIMENTS OF THE INVENTION

Reference will now be made in detail to preferred embodiments of the invention. Examples of which are illustrated in the following example section.

To achieve the objects of the invention a bioadhesive pharmaceutical carrier or dosage form is provided which consists essentially of a polymer blend of sodium carboxymethyl cellulose and xanthan gum or sodium alginate in which is dispersed a pharmaceutical active. The pharmaceutical carrier or dosage form of the invention can be in semi-solid (e.g. gel) or solid (e.g. powder) form. In preferred embodiments the carrier or dosage form is a semi-solid comprising, in weight by weight of the total product, of from about 0.25 to 25%, more preferably about 10 to 20% and most preferably about 15 to 20% of each of sodium carboxymethyl cellulose and xanthan gum or about 0.25 to 25%, more preferably 10 to 20% and most preferably 10 to 15% sodium alginate as a substitute for the xanthan gum. In other preferred embodiments of a solid form the carrier comprises in weight by weight of the total product of from about 0.25 to 50%, more preferably 15 to 25% and most preferably 15 to 20% of each of sodium carboxymethyl cellulose and xanthan gum or about 0.25 to 50%, more preferably about 15 to 25% and most preferably 20 to 25% or sodium alginate as a substitute for xanthan gum.

The bioadhesive pharmaceutical carrier is a single matrix in the form of a liquid gel. This form is very convenient since it can be molded to the area of application and also can be appropriately metered in amounts and dosages as needed. This dosage form is therefore conveniently adhered to the mucous membranes in the mouth including, for example, cheeks, gums, tongue, pallet, etc., as well as to the lips. This dosage form is also applicable to the rectal, anal, vaginal, or nasal tissues, as well as the ear and eye areas of the body. Further, the dosage form can be applied in a powder or sprinkle form which gels upon contact with body fluids and bioadheres to the immediate body area.

The gel dosage form of the present invention has a smooth feel and is non-gritty for comfortable application to the intended areas of the body. Further, the gel dosage form requires no alcohol be present which is particularly suitable for use in treating children or sensitive areas such as inflamed, raw or sore spots (e.g., canker sores, fever blisters, hemorrhoids, etc.).

In addition to the polymer blend of sodium carboxymethyl cellulose and xanthan gum or sodium alginate, it may be desirable to add a diluent or vehicle material which can be water soluble or have low water solubility be water insoluble. Preferred water soluble vehicle materials include glycerin, propylene glycol, dioxolanes, glycerol, glycofurol, dimethylacetamide, ethyl lactate, alcohols, glycols and sorbitols. Preferably the water soluble vehicle material is a polyethylene glycol wit a molecular weight of between 300 and 20,000 or mixtures thereof. Other preferred vehicle materials include viscous vehicle materials which have low water solubility or are water insoluble and are selected from the group consisting of USP and NF oils (e.g. mineral oil, castor oil, corn oil, mineral oil, peanut oil, sesame oil and waxes), lanolin, hydrophilic petrolatum, anhydrous lanolin, lecithin, ethyl oleate, isopropyl myristate, benzyl benzoate, petrolatum, cocoa butter. Generally, addition of water soluble vehicle materials will quicken release of the active material and water insoluble vehicle materials will retard release of the active material from the bioadhesive dosage form.

Various pharmaceutical actives can be included in the bioadhesive dosage form. Examples of such pharmaceutical actives include but are not limited to anesthetics including benzocaine, pramoxine, dibucaine, diclonine, lidocaine, mepiracaine, prilocaine, and tetracaine; demulcents (including benzoin, acacia, tragacanth, polyvinyl alcohol and glycerin; analgesics including opiate analgesics (e.g. codeine or hydrocodone), non-opiate analgesics, (e.g. meperidine or methadone), non-narcotic analgesics including acetaminophen and NSAIDS (e.g. s-ibuprofen, ketoprofen, fenoprofen, indomethacin, meclofenamate, mefenamic acid, naproxen, phenylbutazone, piroxicam, tolmetin, sulindac, and dimethyl sulfoxide), astringents including calamine, zinc oxide, tannic acid, hamamelis water, zinc sulfate; wound cleansers (e.g. benzalkonium chloride, carbamide peroxide, tannic acid, salicylic acid, triclosan, benzoyl peroxide, and boric acid); natural or synthetic steroids including triamcinolone acetonide, prednisone, beclomethasone dipropionate; asthmatic drugs including terbutaline sulfate, albuterol, leukotriene receptor antagonists; electrolytes, metals and minerals; antianxiety and antidepressant agents; antimicrobial and antiviral agents (e.g. acyclovir, neomycin, bacitracin, polymyxin B, vidarabine, trifluridine, zidovucine, methenamine, nonoxynol sulfonamides and other antibiotics); wound healing agents (e.g. fish oils, shark liver oil, castor oil, sucralfate and liver yeast cell derivatives); antihistamines (e.g. diphenhydramine, promethazine, cromolyn, cyproheptadine, and azatadine); immune suppression agents; cholesterol lowering agents; cardiac and high blood pressure agents; menthol; camphor; ibuprofen and menthol; benzocaine and triamcinolone acetonide; and mixtures thereof.

Other pharmaceutically acceptable excipients may be added to the bioadhesive gel dosage form such as, for example, acidifying agents; antimicrobial preservatives; antioxidants; buffering agents; colorings; flavors; perfumes; sweeteners; and mixtures thereof.

The bioadhesive dosage form of the invention can take on various forms including, but not limited to, powders, gels, creams, ointments, suppositories, films, tablets, capsules, caplets, implants, emulsions, aerosols and sprays. Examples of applications include nasal sprays or gels, gel contraceptives and anti-cancer oncological treatments for direct application to affected body areas (e.g., cervix). The dosage form is particularly suited for problematical drugs since smaller dosage amounts can be applied and concentrated at the site of action and released in a metered and controlled manner.

A more preferred embodiment of the invention is a teething gel product or product for treating canker sores (i.e., fever blisters or cold sores) which comprises as a dosage form the bioadhesive carrier of the invention and an anesthetic. Such a teething gel product would also preferably contain flavoring ingredients. The polymeric ingredients of the present invention have an essentially neutral taste and therefore can be advantageously flavored to provide good tasting formulations for oral use. Examples of teething gel produces are included in the Examples section.

The present invention also comprises a method of control releasing pharmaceutical actives comprising incorporating such actives in a bioadhesive pharmaceutical carrier comprising the polymer blend of sodium carboxymethyl cellulose and xanthan gum or sodium alginate as previously discussed. Additional ingredients such as diluents or vehicle materials are also incorporated therein as also previously discussed. The method of control releasing pharmaceutical actives in accordance with the invention comprises the steps of incorporating a pharmaceutical active into a bioadhesive dosage form matrix consisting essentially of a polymer blend of sodium carboxymethyl cellulose and xanthan gum; and administering the dosage form to a patient. In preferred embodiments, the release of the drug material is slowed by adding proportionally more xanthan gum in the polymer blend.

In preferred methods of the invention, the dosage form is administered orally, nasally, rectally, vaginally, ophthalmically, optically or topically. In accordance with the method of the invention, the dosage form is preferably administered directly to the site of action. More preferably, the dosage form is administered orally and most preferably to the lips, mouth or gum area.

In accordance with the invention, the pharmaceutical additive can be released in a effective amount over a period of time which will provide effective and efficient pharmaceutical action and reduce the amount of toxicity of the pharmaceutical active dose utilize. Such metered action is particularly useful in administering pharmaceutical compositions which may have acute toxicity at higher dosing levels. The fact that the present invention is intended for topical administration directly to the site of action would also require less amounts of the pharmaceutical additive to be used than would a systemic administration of a pharmaceutical.

In accordance with the methods of the invention, the dosage form may be a teething gel which is directly administered to the gums of a teething child. The anesthetic included in such a teething gel may be selected from the group consisting of benzocaine, pramoxine, dibucaine, diclonine, lidocaine, mepivacaine, prilocaine, procaine, tetracaine, and dimethisoquin their pharmaceutically acceptable salts and combinations thereof.

In use, the bioadhesive gel of the present invention provides a temporary adhesive of the gel dosage form to the intended site of action, e.g., mucous membrane. The body moisture present at the site of action initially provides adhesive properties to the bioadhesive gel matrix, but upon saturation the gel adhesive bond diminishes and breaks down. After time the polymer matrix diffuses away and the mucal surface returns to normal.

EXAMPLES

The invention will now be illustrated by examples. The examples are not intended to be limiting of the scope of the present invention but read in conjunction with the detailed and general description above, provide further understanding of the present invention and an outline of a process for preparing the compositions of the invention and methods of practicing the invention.

| Ingredients | Percentage |
|---|---|
| Na CMC | 10 |
| Xanthan Gum | 10 |
| Benzocaine | 7.5 |
| Polyethylene Glycol (PEG 400) | 58 |
| Polyethylene Glycol (PEG 3350) | 14.5 |
| Prepared at 85° C. | |

General Procedure

The PEGs are liquified by stirring and heating. The polymers, actives and inactives are added while either stirring above the melting point of the polymer or at cooler or room temperatures, depending upon the stability, solubility and glass transition temperature of the ingredients used.

The formulation of Example I is prepared by adding with stirring Na CMC and xanthan gum to a clear solution (65° C.) of PEG 600 and PEG 3350. The temperature was slowly increased with stirring to 85° C. This temperature was maintained for one hour to swell and wet the polymer surfaces. The heat was removed and the mixture was allowed to cool. At 45° C. and with constant stirring, the benzocaine was added. The product was allowed to cool. When congealing or gelling occurred, the stirring was stopped and the gel product packaged into tubes and ointment jars.

In other formulations, the flavors, colors, sweeteners, preservatives and glycerine were added together and introduced into the cooling PEG-polymer mixture at 50° C.

EXAMPLES II–XI

The following examples are prepared in accordance with the procedures of Example I utilizing the following formulations with percentage of ingredients indicated for each example:

| Ingredients | II | III | IV | V | VI |
|---|---|---|---|---|---|
| Glycerine | 10 | 10 | 10 | 10 | 10 |
| Na CMC | 5 | 5 | 5 | 5 | 20 |
| Xanthan gum | 5 | 5 | 15 | 15 | 5 |
| Benzocaine | 7.5 | 7.5 | 7.5 | 7.5 | 7.5 |
| Flavoring | 0.15 | 0.15 | 0.15 | 0.15 | 0.15 |
| Na saccharin | 0.5 | 0.5 | 0.5 | 0.5 | 0.5 |
| Methyl paraben | 0.1 | 0.1 | 0.1 | 0.1 | 0.1 |
| PEG 600 | 57.4 | 57.4 | 49.4 | 49.4 | 45.4 |
| PEG 3350 | 14.4 | 14.4 | 12.4 | 12.4 | 11.35 |
| Temperature (°C.) | 65 | 85 | 65 | 85 | 65 |

| Ingredients | VII | VIII | IX | X | XI |
|---|---|---|---|---|---|
| Glycerine | 10 | 10 | 10 | 10 | 10 |
| Na CMC | 20 | 20 | 20 | 20 | 15 |
| Xanthan gum | 5 | 15 | 15 | 20 | 20 |
| Benzocaine | 7.5 | 7.5 | 7.5 | 7.5 | 7.5 |
| Flavoring | 0.15 | 0.15 | 0.15 | 0.15 | 0.15 |
| Na saccharin | 0.5 | 0.5 | 0.5 | 0.5 | 0.5 |
| Methyl paraben | 0.1 | 0.1 | 0.1 | 0.1 | 0.1 |
| PEG 600 | 45.4 | 37.4 | 37.4 | 33.4 | 31.4 |
| PEG 3350 | 11.35 | 9.35 | 9.35 | 8.4 | 9.4 |
| Temperature (°C.) | 85 | 65 | 85 | 65 | 85 |

| Ingredients | XII | XIII | XIV |
|---|---|---|---|
| Glycerine | 10 | 10 | 10 |
| Na CMC | 20 | 20 | 15 |
| Xanthan gum | 15 | 20 | 20 |
| Benzocaine | 7.5 | 7.5 | 7.5 |
| Flavoring | 0.15 | 0.15 | 0.15 |
| Na saccharin | 0.5 | 0.5 | 0.5 |
| Methyl paraben | 0.1 | 0.1 | 0.1 |
| PEG 600 | 35.4 | 31.4 | 35.4 |
| PEG 3350 | 8.9 | 7.9 | 8.9 |
| Temperature (°C.) | 65 | 65 | 65 |

| Ingredients | XV | XVI | XVII |
|---|---|---|---|
| Na CMC | 10 | 10 | 10 |
| Na Alginate | 20 | 20 | 15 |
| Benzocaine | 7.5 | 7.5 | 7.5 |
| PEG 400 | 58.0 | 50.0 | 58.0 |
| PEG 3350 | 14.5 | 12.5 | 14.5 |
| Temperature (°C.) | 85 | 85 | 85 |

The benzocaine (active) release from the gel matrix examples of the invention is reported in Table 1 as a percentage of benzocaine released over 180 minutes for each of the formulations of Examples II–XIV. It is seen, for example, that Example II shows the quickest release, whereas Example XIII shows the slowest release, but virtually all of the benzocaine has been released by 180 minutes. It is apparent that such releases may be controlled for various applications by varying the particular formulations utilized.

Table 2 provides the results of a simulated adhesion of the gel of the invention to human gums by measuring the adhesion strength of the gels of the invention of Examples II–XII to glass. The gels of the invention are also favorably compared to control gels and a commercial product identified by its trademark ORABASE B. The results provided in Table 2 demonstrate the excellent wet adhesion strength of the gels of the invention even after soaking in normal saline solution for three minutes.

TABLE 1

Benzocaine release from the gels of the invention into normal saline. These gels contain 7.5% benzocaine; a highly water soluble drug.
Percentage of benzocaine release from the Gel vs. Time.

| Time (minutes)/ Formula (Example | II | III | IV | V | VI | VII | VIII | IX |
|---|---|---|---|---|---|---|---|---|
| 5 | 30 | 21 | 18 | 15 | 14 | 14 | 11 | 12 |
| 10 | 50 | 47 | 32 | 30 | 27 | 26 | 22 | 23 |
| 15 | 71 | 65 | 43 | 41 | 35 | 36 | 30 | 31 |
| 30 | 95 | 94 | 65 | 65 | 60 | 69 | 50 | 52 |
| 60 | 100 | 100 | 88 | 88 | 85 | 95 | 78 | 78 |
| 120 | | | 100 | 100 | 100 | 100 | 100 | 100 |
| 180 | | | | | | | | |

| Time (minutes)/ Formula (Example | X | XI | XII | XIII | XIV | XV | XVI | XVII |
|---|---|---|---|---|---|---|---|---|

TABLE 1-continued

Benzocaine release from the gels of the invention into normal saline. These gels contain 7.5% benzocaine; a highly water soluble drug. Percentage of benzocaine release from the Gel vs. Time.

|     |     |     |     |     |     |     |     |     |
| --- | --- | --- | --- | --- | --- | --- | --- | --- |
| 5   | 8   | 8   | 7   | 6   | 7   | 6   | 5   | 7   |
| 10  | 16  | 16  | 14  | 12  | 14  | 12  | 7   | 14  |
| 15  | 21  | 22  | 22  | 19  | 21  | 17  | 11  | 21  |
| 30  | 40  | 40  | 38  | 34  | 37  | 36  | 24  | 41  |
| 60  | 60  | 66  | 61  | 57  | 60  | 57  | 39  | 57  |
| 120 | 85  | 86  | —   | —   | —   | 67  | 51  | 83  |
| 180 | 100 | 100 | 100 | 100 | 100 | 100 | 100 | 100 |

TABLE 2

Adhesion strength of gels to glass. Simulated adhesion of the gel to human gums.

| Ingredients Ex. No. | Adhesion (as is) (in kg) | Adhesion: Peak load strength (in kg) after a soaking time in minutes in normal saline | | |
| --- | --- | --- | --- | --- |
| | | 1 min. | 2 min. | 3 min. |
| II | 0.48 | 0.44 | 0.69 | 0.58 |
| III | 0.33 | 0.62 | 0.5 | 0.4 |
| IV | 0.42 | 0.78 | 0.68 | 0.47 |
| V | 0.42 | 0.61 | 0.71 | 0.67 |
| VI | 0.76 | 0.76 | 0.7 | 0.64 |
| VII | 0.44 | 0.61 | 0.78 | 0,75 |
| VIII | 0.96 | 0.81 | 0.8 | 0.78 |
| IX | 1.00 | 0.93 | 0.94 | 0.98 |
| X | 0.71 | 1.01 | 0.73 | 0.93 |
| XI | 0.61 | 1.04 | 0.9 | 0.85 |
| XII | 0.66 | 0.74 | 0.69 | 0.63 |
| Control | 0.60 | 0.41 | 0.29 | LT 0.1 |
| ORABASE B* | 0.51 | 0.98 | 0.92 | 0.96 |

*Trademark;
LT = less than
ORABASE B is a 20% benzocaine containing dental paste of gelatin, pectin, and sodium carboxymethyl cellulose in a polyethylene and mineral oil base.
Control is a 7.5% benzocaine containing glycerine polyethylene based gel.

The scope of the present invention is not limited by the description, examples, and suggested uses herein, and modifications can be made without departing from the spirit of the invention. For example, the bioadhesive gel matrix of the invention can be used as a carrier for vitamin or mineral products or other nutrients for which a sustained release to a particular area or site is desirable.

Application of the compositions and methods of the present invention for medical and pharmaceutical uses can be accomplished by any clinical, medical, and pharmaceutical method and technique as would be presently or prospectively known to those skilled in the art. For example, the bioadhesive composition of the present invention may be employed in various other dosage forms including, without limitation, tablets, ointments, creams, suppositories, injection molded particles or tablets, films, emulsions, aerosols, spray congealed particles and implants. Thus, it is intended that the present invention cover the modifications and variations of this invention provided that they come within the scope of the appended claims and their equivalents.

What is claimed is:

1. A bioadhesive pharmaceutical gel, consisting essentially of:

a therapeutically effective amount of an antidepressant agent;

about 0.25 to about 25 percent by weight sodium carboxymethyl cellulose;

about 0.25 to about 25 percent by weight xanthan gum or sodium alginate and;

diluent selected from the group consisting of glycerin, propylene glycol, dioxolanes, glycerol, glycofurol, dimethylacetamide, ethyl lactate, alcohols, glycols, sorbitols, USP oils, NF oils, lecithin, lanolin, ethyl oleate, isopropyl myristate, benzyl benzoate, petrolatum, cocoa butter and mixtures thereof.

2. The bioadhesive of claim 1, further comprising pharmaceutically acceptable excipients selected from the group consisting of acidifying agents, antimicrobial preservatives, antioxidants, buffering agents, colorings, flavors, perfumes, sweeteners, and mixtures thereof.

3. The bioadhesive of claim 2 wherein the diluent is selected from the group consisting of glycerin, propylene glycol, dioxolanes, glycerol, glycofurol, dimethylacetamide, ethyl lactate, alcohols, glycols, sorbitols and mixtures thereof.

4. The bioadhesive of claim 3 wherein the diluent is a polyethylene glycol with a molecular weight of between 300 and 20,000 or mixtures thereof.

5. The bioadhesive of claim 1 comprising from about 10 to about 20 weight percent of sodium carboxymethyl cellulose and from about 10 to about 20 weight percent of xanthan gum or sodium alginate.

6. The bioadhesive of claim 5 comprising from about 15 to about 20 weight percent of sodium carboxymethyl cellulose and about 15 to about 20 weight percent of xanthan gum or about 10 to about 15 weight percent sodium alginate.

7. A method of orally administering the bioadhesive of claim 1 to a patient.

* * * * *